United States Patent
Shinzaki et al.

[11] Patent Number: 5,621,516
[45] Date of Patent: Apr. 15, 1997

[54] OPTICAL DEVICE FOR FORMING AN IMAGE OF AN UNEVEN SURFACE

[75] Inventors: Takashi Shinzaki; Satoshi Iwata, both of Kanagawa, Japan

[73] Assignee: Fujitsu Limited, Kawasaki, Japan

[21] Appl. No.: 371,808

[22] Filed: Jan. 12, 1995

[30] Foreign Application Priority Data

Feb. 4, 1994 [JP] Japan .................................. 6-012425

[51] Int. Cl.$^6$ ..................................................... G06K 9/74
[52] U.S. Cl. .......................... 356/71; 382/124; 382/125; 382/126; 382/127
[58] Field of Search .................... 356/71; 382/124–127

[56] References Cited

U.S. PATENT DOCUMENTS

| | | | |
|---|---|---|---|
| 4,681,435 | 7/1987 | Kubota et al. | 356/71 |
| 4,924,085 | 5/1990 | Kato et al. | 356/71 |
| 5,088,817 | 2/1992 | Igaki et al. | 356/71 |
| 5,416,573 | 5/1995 | Sartor, Jr. | 356/71 |

FOREIGN PATENT DOCUMENTS

| | | | |
|---|---|---|---|
| 60-050406 | 3/1985 | Japan | 356/71 |
| 63-211468 | 9/1988 | Japan . | |

OTHER PUBLICATIONS

Fujitsu Scientific and Tec. J., vol. 25, No. 4, 1989 Kawasaki, JP, pp. 287–296, XP 000103957 T. Shinzaki et al. "Holographic Fingerprint Sensor", Section 4.3 Optimizing the lighting angle *Figures 10–12*.

*Primary Examiner*—Frank Gonzalez
*Assistant Examiner*—Jason D. Eisenberg
*Attorney, Agent, or Firm*—Staas & Halsey

[57] ABSTRACT

An optical device for forming an image of an uneven surface, including a plane-parallel plate with a pair of parallel plane surfaces which is made of a transparent material having a refractive index larger than that of water and transparent to illuminating light. An uneven object (object having an uneven surface) is placed in close contact with one plane surface of the plane-parallel plate. A light source illuminates the uneven object through the plane-parallel plate. Among light rays scattered back into the plane-parallel plate by the uneven object and totally reflected at the other plane surface of the plane-parallel plate, only light that is totally reflected at an angle larger than the critical angle at the boundary between the plane-parallel plate and water is taken in by an image-forming device.

20 Claims, 8 Drawing Sheets

OPTICAL DEVICE FOR FORMING AN IMAGE OF AN UNEVEN SURFACE

BACKGROUND OF THE INVENTION

1. Field of the Invention

The present invention relates to an apparatus for optically reading information directly from an uneven surface, for example, the inner surface of a fingertip when a fingerprint is to be taken, without the need of applying ink or the like to the surface.

2. Description of the Related Art

FIG. 14 in the accompanying drawings shows a conventional technique for taking a fingerprint. As illustrated in the figure, with the fingertip pressed against the surface 101a of a transparent plane-parallel plate 101, e.g., glass plate, the inner surface 50 of the fingertip is illuminated by a light source 102 disposed below the reverse surface 101b of the plane-parallel plate 101. In this case, light that is scattered by recesses the fingertip inner surface 50, which are not in contact with the surface 101a of the plane-parallel plate 101, enters the plane-parallel plate 101 after passing through an air layer.

Accordingly, the scattered light travels through the plane-parallel plate 101 at an angle smaller than the critical angle, as shown by the broken line, and hence passes through the reverse surface 101b of the plane-parallel plate 101, which is in contact with an air layer, and emerges into the air without being totally reflected at the reverse surface 101b.

However, light that is scattered by projections on the fingertip inner surface 50, which are in close contact with the surface 101a of the plane-parallel plate 101, travels through the plane-parallel plate 101 in all directions. Light that reaches the reverse surface 101b of the plane-parallel plate 101 at an angle larger than the critical angle is totally reflected back into the plane-parallel plate 101. Therefore, only the totally reflected light is taken in by an optical system comprising optical elements 103 to 107, to form an image on the image receiving surface of a solid-state imaging device 106, for example, thereby enabling dactylographic information to be read from the fingertip inner surface 50.

However, if there is water, e.g., sweat, rain, etc., (hereinafter referred to simply as "water") 51 in a recess in the fingertip inner surface 50, since the refractive index of water 51 is larger than that of the air, light that emerges from the water 51 travels through the plane-parallel plate 101 at an angle larger than in the case of incidence from the air, as shown by the arrow A. Accordingly, the scattered light from the recesses is totally reflected at the reverse surface 101b of the plane-parallel plate 101, thus making it impossible to accurately read dactylographic information from the fingertip inner surface 50.

When a trough portion of the fingertip inner surface 50 is filled with sweat, a false ridge appears between a pair of adjacent ridges on the fingertip inner surface 50 to form a bridge between the adjacent ridges. As a result, troughs which are filled with sweat are erroneously detected as ridges, as shown by reference symbol B in FIG. 15.

When dactylographic features are extracted from information read from the fingertip inner surface 50 wet with sweat as described above, bridge portions (indicated by B) are undesirably recorded as branch points. Since "bridges" produced by sweat have no reproducibility, if they are recorded as features, the fingerprint collating efficiency is lowered.

FIG. 16 shows one example of conventional approaches to cope with the above-described problem. As illustrated in the figure, light that is scattered back into a transparent member 201 by projections on the fingertip inner surface and then emerges into the air from a side surface of the transparent member 201 is detected at a position (in the hatched region 300) that cannot be reached by light that enters the transparent member 201 through a water layer filling a recess in the fingertip inner surface, and the detected light is subjected to image formation, thereby reading dactylographic information. In FIG. 16, reference numeral 202 denotes a light source, and 207 a camera [for example, see Japanese Patent Application Laid-Open (KOKAI) No. 63-211468 (1988)].

However, when an image-forming optical system is disposed in the region 300 that can be reached only by light that is scattered back into the transparent member 201 by projections on the fingertip inner surface and then emerges into the air from the transparent member 201, the image-forming optical system must be tilted with respect to the transparent member 201. Therefore, the conventional technique suffers from the disadvantage that a troublesome operation is required to handle the apparatus, for example, positional adjustment in actual use, and thus the conventional apparatus is difficult to use. In addition, the transparent member 201, which is formed, for example, from a prism or a plane-parallel plate, must be large in size. In the ease of a plane-parallel plate, a thickness of 17.47 mm or more is required.

SUMMARY OF THE INVENTION

An object of the present invention is to provide an optical device for forming an uneven surface which is capable of accurate reading independently of the presence of water, e.g., sweat, in a recess in the uneven surface, and is easy to handle and which can be arranged in a compact form.

Other objects and advantages of the present invention will become apparent from the following detailed description of illustrated embodiments of the invention.

According to the present invention, there is provided an uneven surface reading apparatus including a plane-parallel plate with a pair of parallel plane surfaces and which is made of a transparent material having a refractive index larger than that of water and is transparent to illuminating light. An uneven object is placed in close contact with one plane surface of the plane-parallel plate. A light source illuminates the uneven object through the plane-parallel plate. Among light rays scattered back into the plane-parallel plate by the uneven object and totally reflected at the other plane surface of the plane-parallel plate, only light that is totally reflected at an angle larger than the critical angle at the boundary between the plane-parallel plate and water is taken in by an image-forming device to form an image of the uneven object.

In addition, there is provided an uneven surface reading apparatus including a plane-parallel plate with a pair of parallel plane surfaces which is made of a transparent material having a refractive index larger than that of water and transparent to illuminating light. An uneven object is placed in close contact with one plane surface of the plane-parallel plate. A trap transparent member is disposed in close contact with the other plane surface of the plane-parallel plate. The trap transparent member is made of a transparent material having a refractive index intermediate between those of water and the plane-parallel plate and transparent to illuminating light. A light source illuminates the uneven object through the plane-parallel plate. An image-forming device forms an image of the uneven object by taking in only light that is scattered back into the plane-parallel plate by the uneven object and totally reflected at the boundary surface of the plane-parallel plate with the trap transparent member.

BRIEF DESCRIPTION OF THE DRAWINGS

The present invention may be more fully understood from the description of preferred embodiments of the invention set forth below, together with the accompanying drawings, in which.

DESCRIPTION OF THE PREFERRED EMBODIMENTS

Embodiments of the present invention will be described below in detail with reference to the accompanying drawings.

Figure 1:
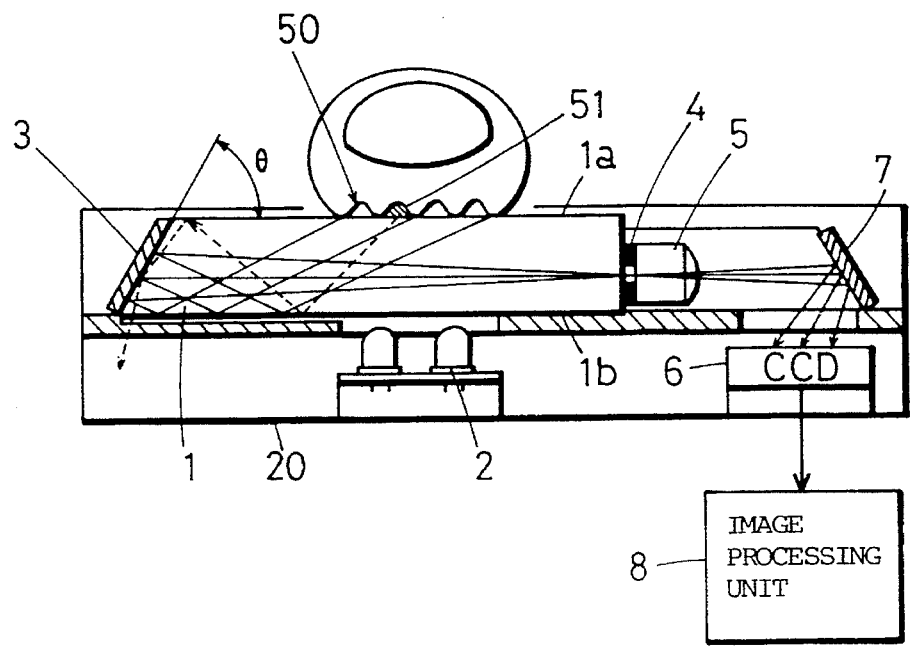
FIG. 1 illustrates the arrangement of a first embodiment of the present invention.

FIG. 1 shows a first embodiment of the present invention. A plane-parallel plate 1 with a pair of parallel plane surfaces 1a and 1b is made of a glass or plastic material which is transparent to illuminating light that is emitted from a light source 2. The plane-parallel plate 1 is designed so that the inner surface 50 of the fingertip as an uneven object is placed in close contact with the top surface 1a of the plane-parallel plate 1.

Below the bottom surface 1b of the plane-parallel plate 1, a light source (e.g., a light-emitting diode) 2 which emits monochromatic light of wavelength 660 nm, for example, is disposed to face upwardly. Thus, the fingertip inner surface 50 placed in close contact with the top surface 1a of the plane-parallel plate 1 is illuminated with light from the light source 2 through the plane-parallel plate 1. It should be noted that the refractive index of the plane-parallel plate 1 is, for example, 1.514 for light of wavelength 660 nm.

One end surface (the left end surface as viewed in the figure) of the plane-parallel plate 1 is tilted at an angle of 77.5 degrees with respect to the plane surfaces 1a and 1b. A plane mirror 3 is provided on the tilted surface so as to face toward the inside of the plane-parallel plate 1.

The other end surface of the plane-parallel plate 1, which is opposite to the tilted surface provided with the plane mirror 3, is perpendicular to both the plane surfaces 1a and 1b. A field stop 4 is provided on this end surface. An image-forming lens 5 is provided at the outside of the field stop 4 with a direction parallel to the plane surfaces 1a and 1b of the plane-parallel plate 1 defined as an optical axis.

A solid-state imaging device 6, e.g., a charge-coupled device (CCD), is disposed with its image receiving surface lying at a position on the optical axis beyond the image-forming lens 5 where an image of the top surface 1a of the plane-parallel plate 1 is formed (i.e., the position where an image of the fingertip inner surface 50 is formed).

A mirror 7 is disposed to bend the optical axis between the image-forming lens 5 and the solid-state imaging device 6. An image processing unit 8 processes an image taken by the solid-state imaging device 6 and reproduces the image on a monitor or the like (not shown). The plane mirror 3, the field stop 4 and the image-forming lens 5 form image forming means to direct light from the plane-parallel plate 1 to the solid state imaging device 6 via the mirror 7.

In the apparatus of this embodiment, arranged as described above, light from the light source 2 illuminates the fingertip inner surface 50 through the plane-parallel plate 1, and light that impinges on the fingertip inner surface 50 is scattered in all directions.

It should be noted that in FIG. 1 hatching for showing the cross-sections of transparent members, e.g., the plane-parallel plate 1, the image-forming lens 5, etc., is omitted with a view to making the optical path easy to see. A casing 20 supports and covers the constituent elements of the uneven surface reading apparatus. In the other embodiments (described later), illustration of the casing 20 is omitted.

Figure 2:
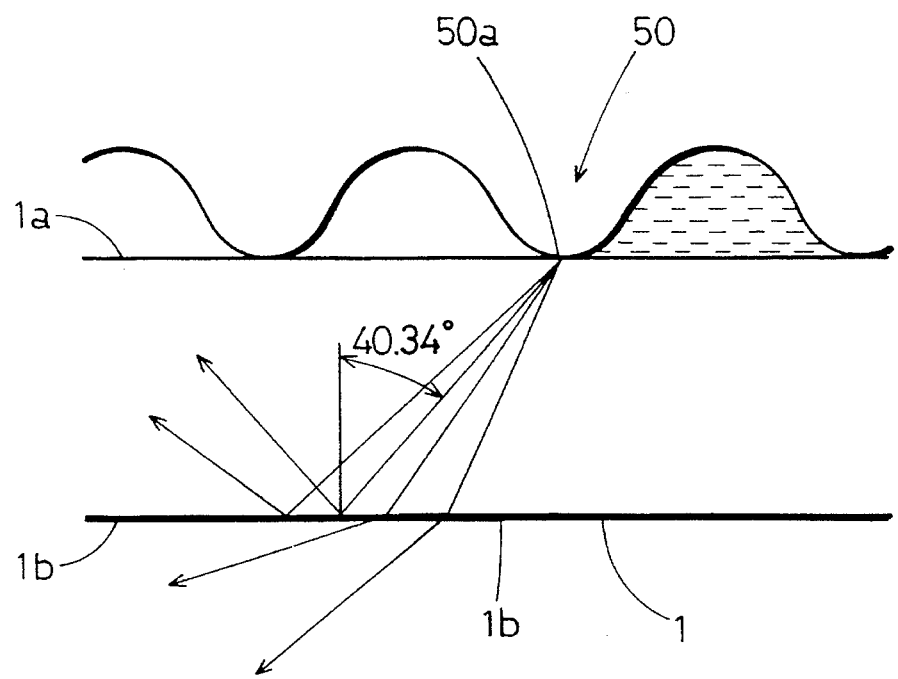
FIG. 2 illustrates the operation of the first embodiment of the present invention.

FIG. 2 shows optical paths of light scattered by a projection on the fingertip inner surface 50, which is placed in close contact with the plane-parallel plate 1. The scattered light travels through the plane-parallel plate 1 in all directions because it does not pass through the air after being scattered by the fingertip inner surface 50.

At the boundary of the bottom surface 1b of the plane-parallel plate 1 with the air layer, light incident on the bottom surface 1b at an angle smaller than the critical angle at the boundary surface between the plane-parallel plate 1 and the air layer emerges into the air from the bottom surface 1b, whereas light incident on the bottom surface 1b at an angle larger than the critical angle is totally reflected back into the plane-parallel plate 1. In this embodiment, the critical angle is 41.34 degrees.

Figure 3:
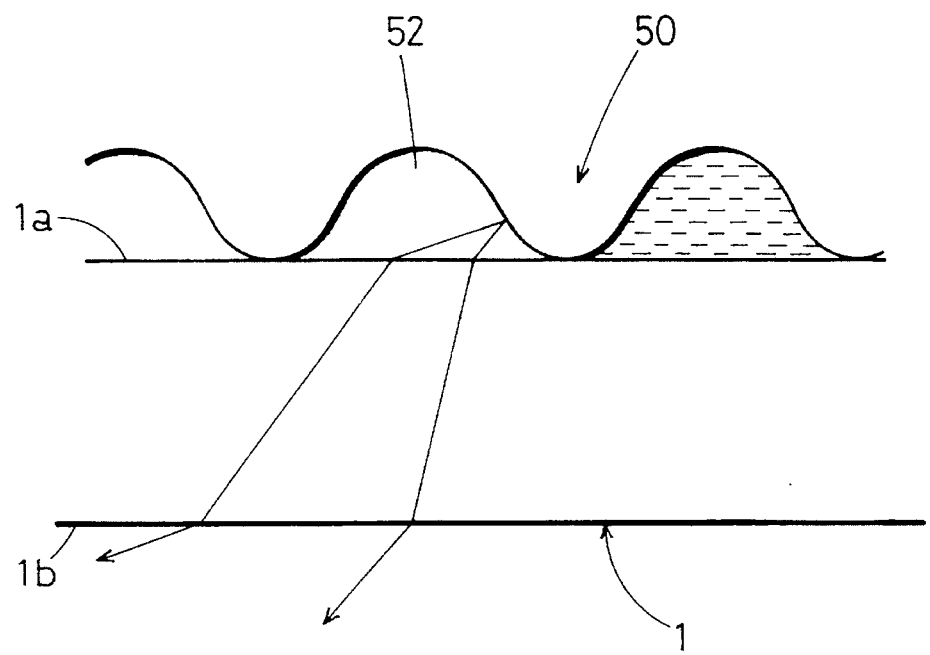
FIG. 3 illustrates the operation of the first embodiment of the present invention.

FIG. 3 shows optical paths of light that is scattered by a recess in the fingertip inner surface 50 where an air layer 52 exists between the fingertip inner surface 50 and the plane-parallel plate 1. The scattered light enters the plane-parallel plate 1 from the air layer 52 through the top surface 1a of the plane-parallel plate 1 and emerges into the air from the bottom surface 1b of the plane-parallel plate 1. Accordingly, the scattered light is not reflected at the bottom surface 1b of the plane-parallel plate 1; all the light emerges into the air.

Figure 4:
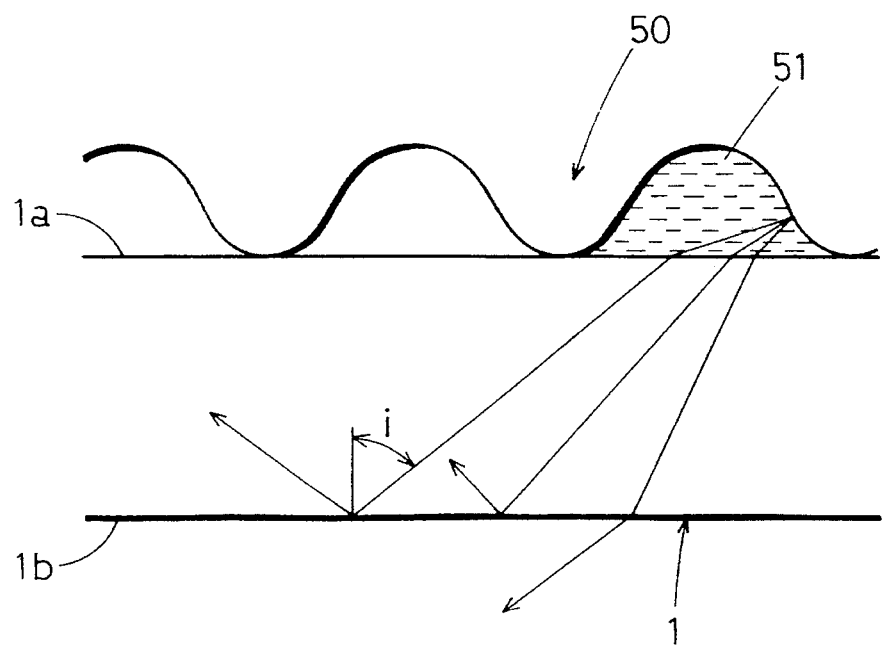
FIG. 4 illustrates the operation of the first embodiment.

FIG. 4 shows optical paths of light in a case where water 51, e.g., sweat or rain, is present in a recess in the fingertip inner surface 50. Assuming that the refractive index of the sweat 51 is 1.34, the critical angle at the boundary surface between the plane-parallel plate 1 and the sweat 51 is 62.3 degrees. Accordingly, light that is scattered by a recess in the fingertip inner surface 50 and enters the plane-parallel plate 1 through the sweat layer 51 reaches the bottom surface 1b of the plane-parallel plate 1 at an incident angle smaller than 62.3 degrees.

In other words, light passing through the sweat layer 51 does not reach the bottom surface 1b of the plane-parallel plate 1 at an incident angle larger than 62.3 degrees. Light that is incident on the bottom surface 1b at an angle i in the range of from 41.34 degrees to 62.3 degrees is totally reflected back into the plane-parallel plate 1 at the bottom surface 1b.

Referring to FIG. 1, since in the apparatus of this embodiment the angle Θ of the tilted surface of the plane mirror 3 is set at 77.5 degrees, light that is incident on the bottom surface 1b of the plane-parallel plate 1 at an angle of 65 degrees and is totally reflected at the bottom surface 1b is reflected by the plane mirror 3 in a direction parallel to the plane surfaces 1a and 1b of the plane-parallel plate 1 so as to reach the field stop 4.

Accordingly, only light that reaches the bottom surface 1b of the plane-parallel plate 1 at an incident angle of about 65 degrees and is totally reflected therefrom is passed through the image-forming lens 5 to form an image on the light receiving surface of the solid-state imaging device 6.

Since light passing through the sweat layer 51 does not impinge on the bottom surface 1b of the plane-parallel plate 1 at an incident angle larger than 62.3 degrees, as has been described above, such light cannot reach the image-forming lens 5 via the plane mirror 3, but only light that is scattered by projections on the fingertip inner surface 50 is subjected to image formation. Accordingly, even if sweat 51 is present in recesses in the fingertip inner surface 50, an image of only projections on the fingertip inner surface 50 is formed on the image receiving surface of the solid-state imaging device 6, and thus dactylographic information can be read accurately.

Since only light that is totally reflected at the bottom surface 1b of the plane-parallel plate 1 and then reflected by the tilted plane mirror 3 toward the other end through the plane-parallel plate 1 is used for image formation, the plane-parallel plate 1 need not be thick. Image formation can be satisfactorily effected even if the thickness of the plane-parallel plate 1 is reduced to 10 mm or less. In addition, since the optical axis of the image-forming light is parallel to the plane surfaces 1a and 1b of the plane-parallel plate 1, layout of the image-forming lens 5 and other optical elements constituting the optical system is facilitated, and it is easy to handle the apparatus.

Figure 5:
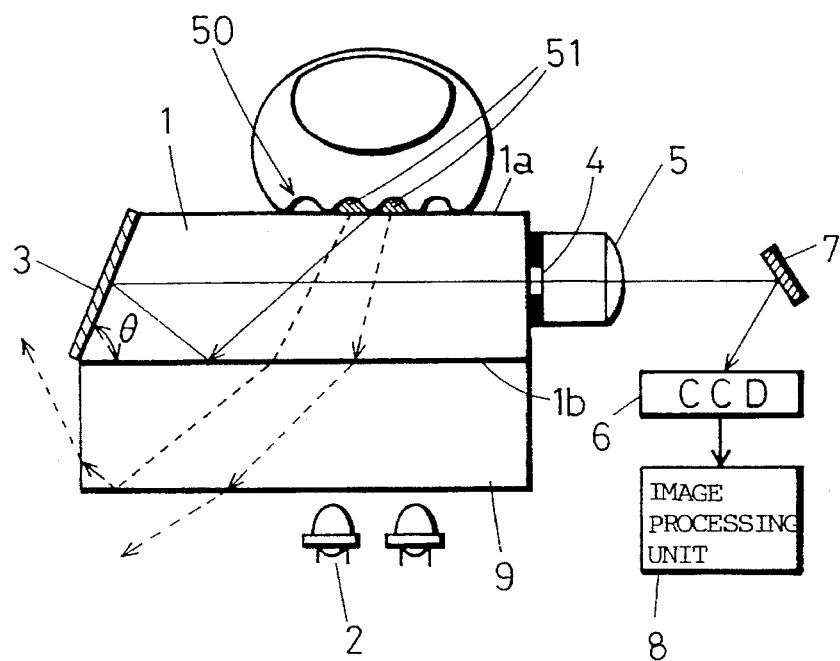
FIG. 5 illustrates the arrangement of a second embodiment of the present invention.

FIG. 5 shows a second embodiment of the present invention. In the second embodiment, a trap transparent member 9, which is a transparent plane-parallel member having a refractive index smaller than that of the plane-parallel plate 1 but larger than that of sweat 51, e.g., 1.45, is cemented securely to the bottom surface 1b of the plane-parallel plate 1.

The light source 2 is disposed directly below the trap transparent member 9. Illuminating light emitted from the light source 2 passes through the trap transparent member 9 and the plane-parallel plate 1 to illuminate the fingertip inner surface 50 placed in close contact with the top surface 1a of the plane-parallel plate 1.

The critical angle at the boundary surface between the plane-parallel plate 1 and the trap transparent member 9, arranged as described above, is 73.3 degrees. On the other hand, light that enters the plane-parallel plate 1 through the sweat layer 51 in recesses in the fingertip inner surface 50 is incident on the bottom surface 1b of the plane-parallel plate 1 at an angle not larger than 62.3 degrees. Therefore, such light is not totally reflected at the bottom surface 1b but enters the trap transparent member 9 and then emerges into the air from the trap transparent member 9, as shown by the broken line in FIG. 5.

Meanwhile, light that is reflected by projections on the fingertip inner surface 50 can impinge on the bottom surface 1b of the plane-parallel plate 1 at an incident angle of 73.3 degrees or more. Accordingly, only light that is scattered by projections on the fingertip inner surface 50, which is placed in close contact with the top surface 1a of the plane-parallel plate 1, is totally reflected at the bottom surface 1b of the plane-parallel plate 1. By taking in only the light totally reflected at the bottom surface 1b for image formation in the same way as in the first embodiment, a pattern of projections (i.e., a ridge pattern) on the fingertip inner surface 50 can be read accurately as dactylographic information.

In this embodiment, unnecessary light is completely separated at the bottom surface 1b of the plane-parallel plate 1. Therefore, an image of higher contrast can be obtained. Assuming that light that impinges on the bottom surface 1b of the plane-parallel plate 1 at an incident angle of 75 degrees is subjected to image formation, the tilt angle Θ of the surface where the plane mirror 3 is provided is set at 82.5 degrees. It should be noted that the refractive index of the trap transparent member 9 should be set at a value intermediate between the refractive index of water and that of the plane-parallel plate 1, and the angle Θ should be varied according to the refractive index of the trap transparent member 9.

Figure 6:
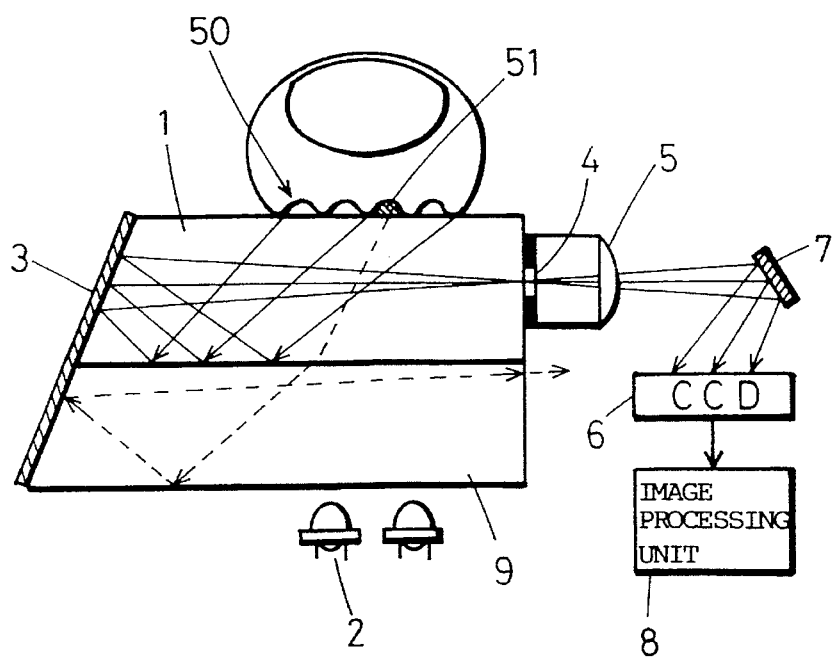
FIG. 6 illustrates the arrangement of a third embodiment of the present invention.
Figure 7:
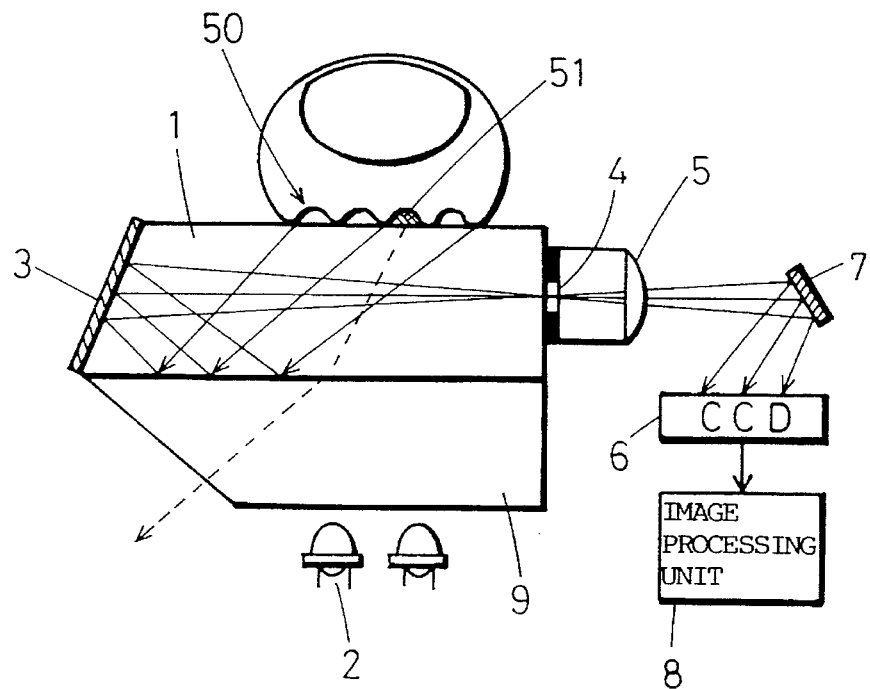
FIG. 7 illustrates the arrangement of a fourth embodiment of the present invention.

FIGS. 6 and 7 show third and fourth embodiments, respectively, of the present invention. In these embodiments, a direction in which light entering the trap transparent member 9 emerges therefrom is specified.

In the third embodiment, shown in FIG. 6, the plane mirror 3 is extended as far as the lower end of the trap transparent member 9 so as to come in close contact with the left end surface (as viewed in the figure) of the trap transparent member 9 as well. As a result, light entering the trap transparent member 9 emerges into the air in a direction approximately parallel to the plane surfaces 1a and 1b of the plane-parallel plate 1, as shown by the broken line in the figure.

In the fourth embodiment, shown in FIG. 7, the left end surface (as viewed in the figure) of the trap transparent member 9 is cut so as to be approximately perpendicular to the optical axis of light entering the trap transparent member 9. Consequently, light entering the trap transparent member 9 emerges into the air from the cut surface at approximately right angles to it.

Figure 8:
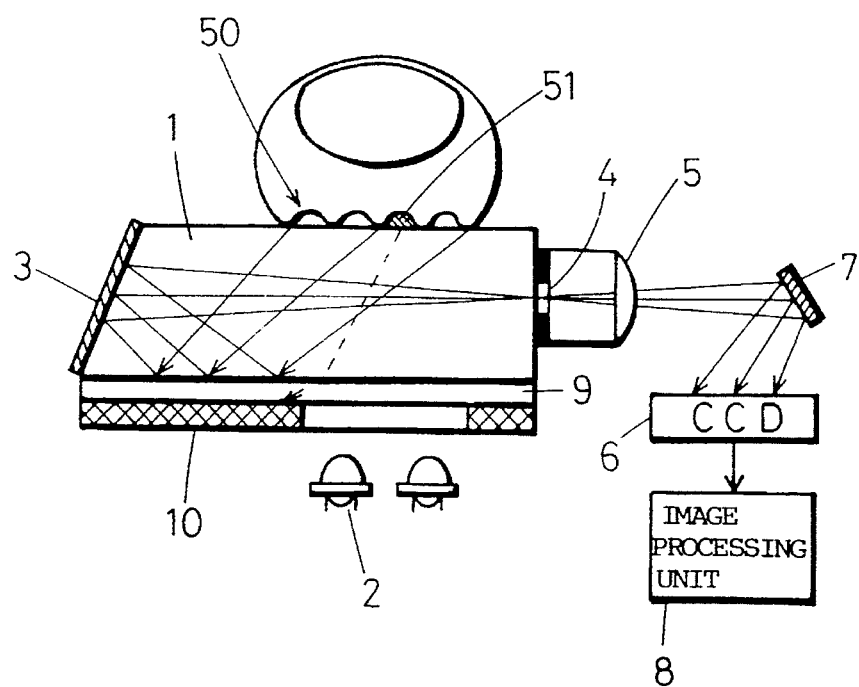
FIG. 8 illustrates the arrangement of a fifth embodiment of the present invention.

FIG. 8 shows a fifth embodiment of the present invention. In this embodiment, a total reflection preventing film 10, e.g., black coating, is provided on the bottom surface of the trap transparent member 9. Since light that reaches the film 10 is not totally reflected, unnecessary light rays will not get mixed in with image-forming rays even if the thickness of the trap transparent member 9 is reduced.

Figure 9:
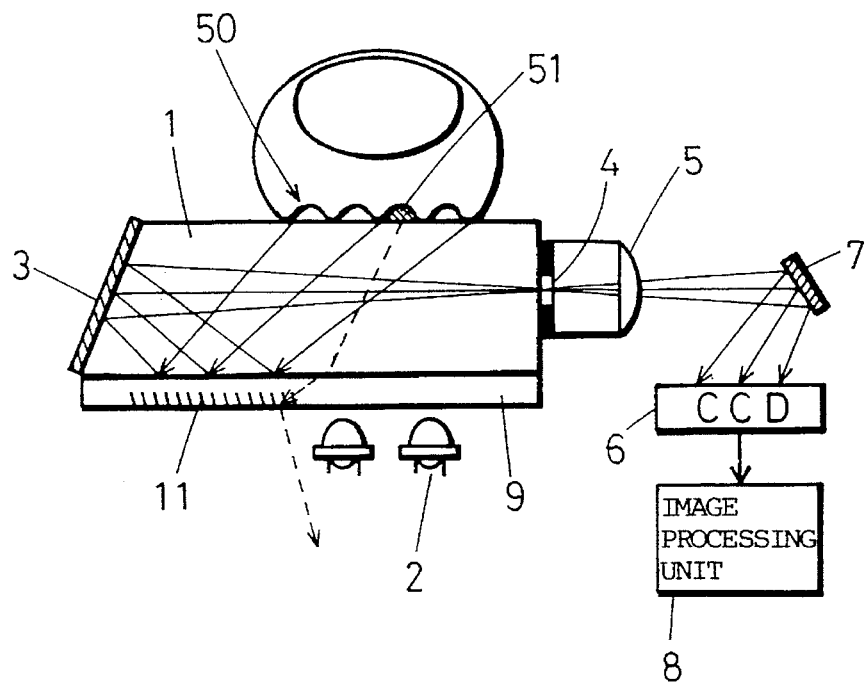
FIG. 9 illustrates the arrangement of a sixth embodiment of the present invention.
Figure 10:
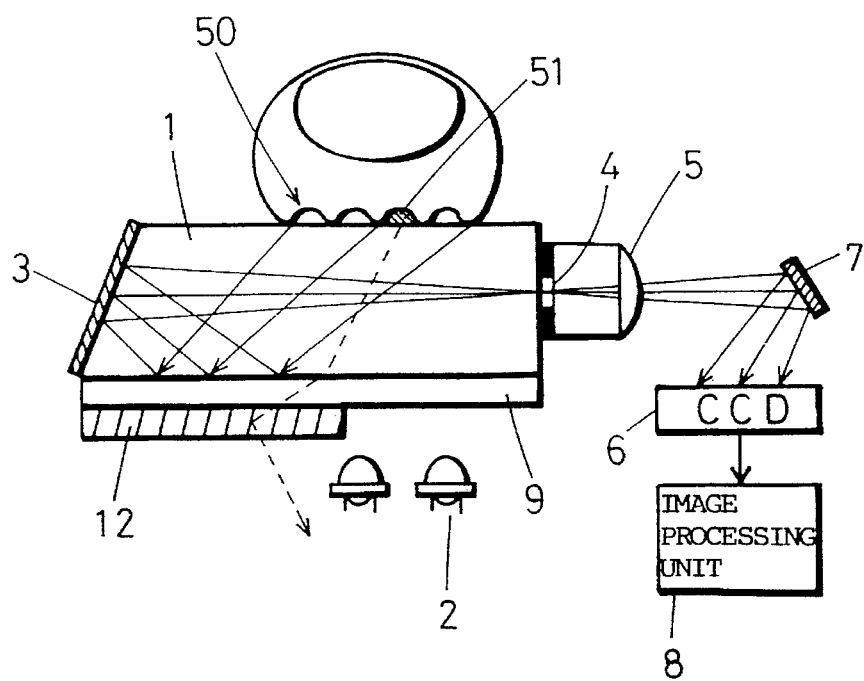
FIG. 10 illustrates the arrangement of a seventh embodiment of the present invention.

FIGS. 9 and 10 show sixth and seventh embodiments, respectively, of the present invention. In these embodiments, a diffraction grating is provided on the bottom surface of the trap transparent member 9, thereby preventing total reflection at the bottom surface of the trap transparent member 9 and also allowing unnecessary light to emerge from the trap transparent member 9 in a predetermined downward direction.

In the sixth embodiment, shown in FIG. 9, a grating 11 is formed on the bottom surface of the trap transparent member 9 as a diffraction grating. In the seventh embodiment, shown in FIG. 10, a surface relief type hologram 12 is cemented securely to the bottom surface of the trap transparent member 9. By disposing a diffraction grating on the bottom surface of the trap transparent member 9 in this way, the thickness of the trap transparent member 9 can be reduced to a considerable extent without giving rise to a problem. Thus, the overall size of the apparatus can be reduced.

Figure 11:
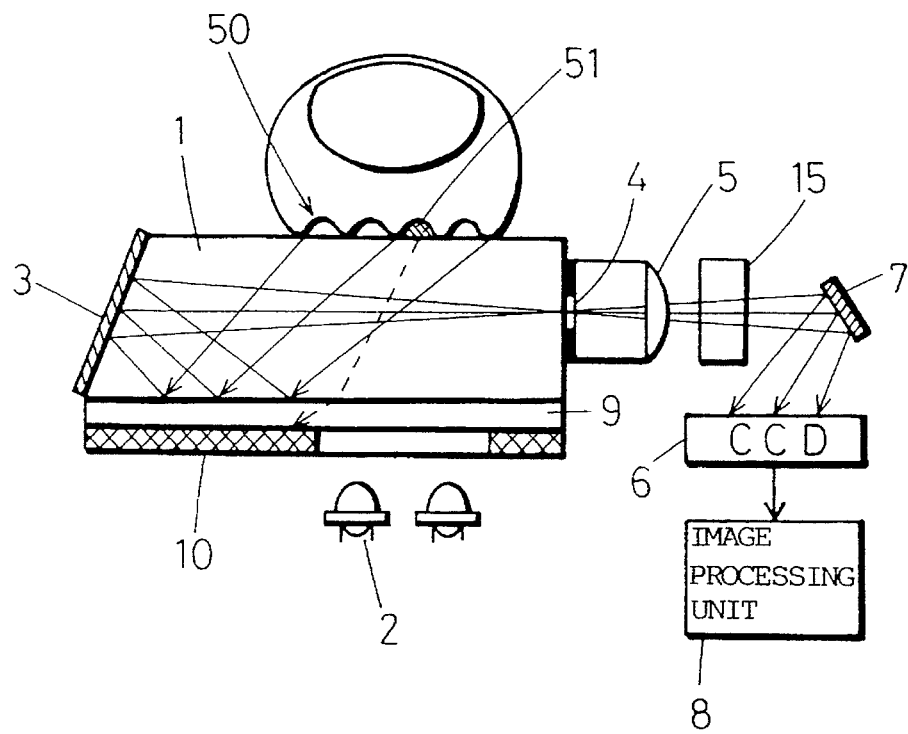
FIG. 11 illustrates the arrangement of an eighth embodiment of the present invention.

FIG. 11 shows an eighth embodiment of the present invention. In this embodiment, a distortion correcting optical system 15 is provided in the image-forming optical system to correct distortion of an image of a pattern of ridges on the fingertip inner surface 50 formed on the light receiving surface of the solid-state imaging device 6.

As the distortion correcting optical system 15, for example, an optical system in which the optical axis of a lens is decentered, or a prism may be used. Thus, image distortion is corrected, and it is possible to read an accurate pattern of ridges on the fingertip inner surface 50. It should be noted that the distortion correcting optical system 15 may be applied to any of the foregoing first to seventh embodiments.

Figure 12:
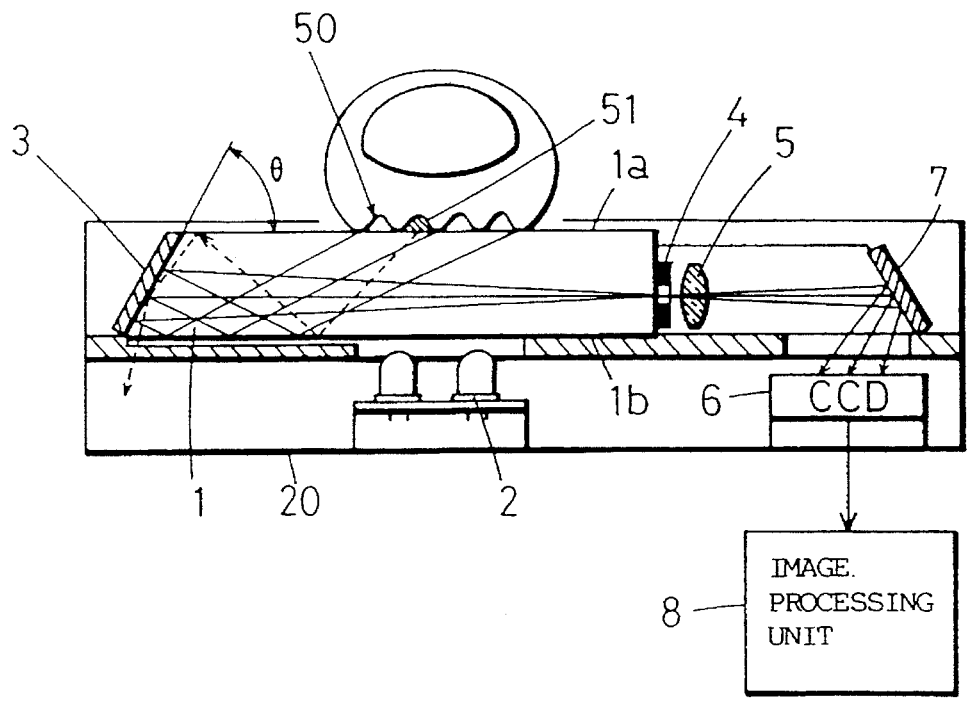
FIG. 12 illustrates the arrangement of a ninth embodiment of the present invention.
Figure 13:
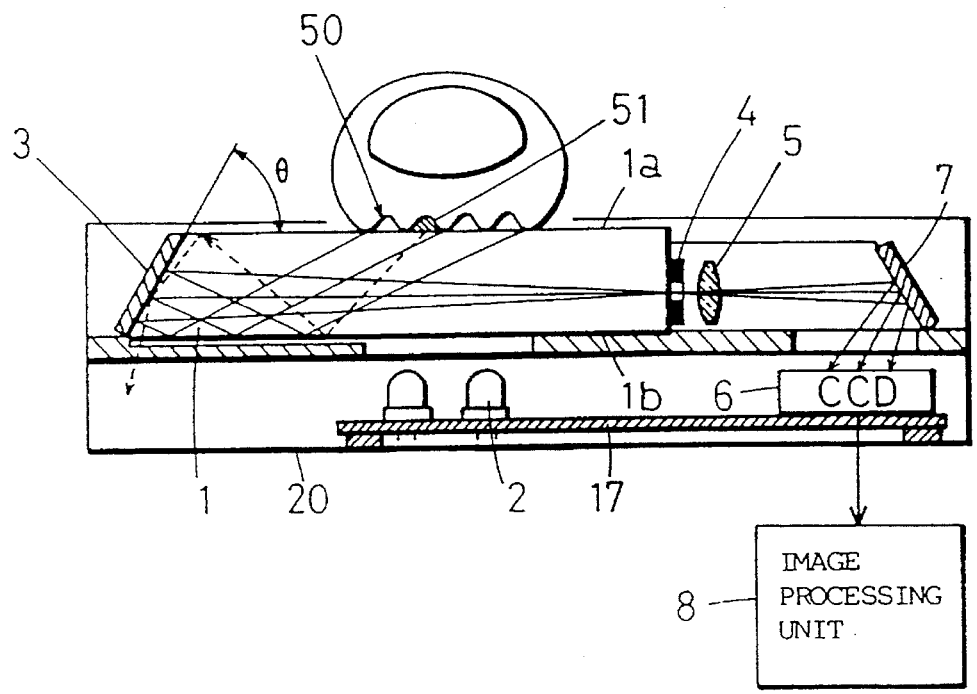
FIG. 13 illustrates the arrangement of a tenth embodiment of the present invention.
Figure 14:
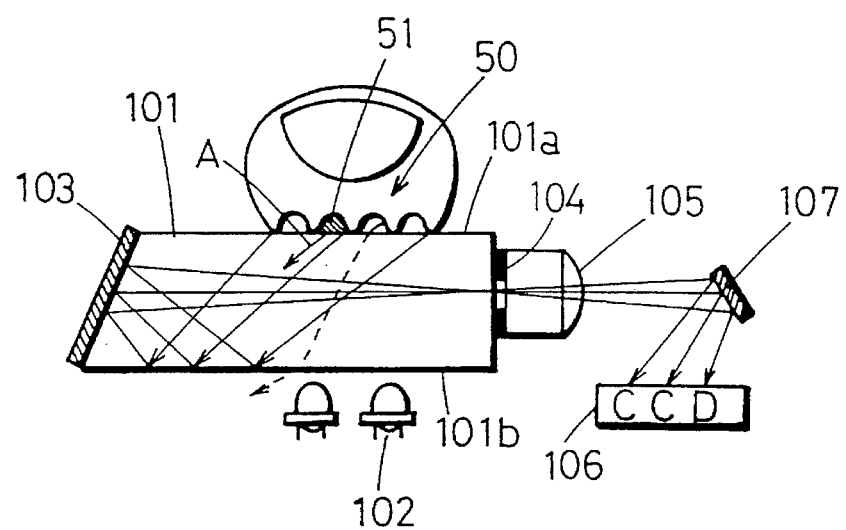
FIG. 14 illustrates the arrangement of a conventional apparatus.
Figure 15:
FIG. 15 shows a result of reading by the conventional apparatus shown in FIG. 14.
Figure 16:
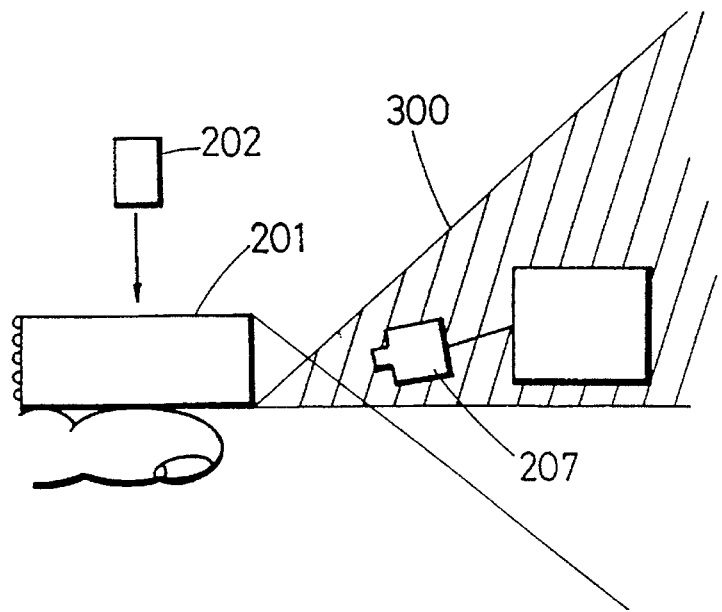
FIG. 16 illustrates the arrangement of another conventional apparatus.

Further, the image-forming lens 5 may be disposed apart from the field stop 4, as shown in a ninth embodiment of the present invention in FIG. 12. The light source 2 and the solid-state imaging device 6 may be attached to the same support plate 17, as shown in a tenth embodiment of the present invention in FIG. 13. These arrangements may also be applied to any of the foregoing first to seventh embodiments.

According to the present invention, an uneven object is placed in close contact with one plane surface of a plane-parallel plate and illuminated with light through the plane-parallel plate, and light that is scattered by the uneven object and totally reflected at the other plane surface of the plane-parallel plate is selectively taken in for image formation. Thus, even if water is present in recesses in the uneven object, an image of only projections on the uneven object can be accurately formed, and required information can be accurately read. Moreover, the optical axis of image-forming light can be set in any desired direction so that the apparatus is easy to handle, for example, in a direction parallel to the plane surfaces of the plane-parallel plate. In addition, the thickness of the plane-parallel plate can be reduced to make the apparatus compact.

If a trap transparent member is disposed in close contact with the second plane surface of the plane-parallel plate where total reflection occurs, light that enters the plane-parallel plate through a water layer present in recesses in the uneven object emerges into the trap transparent member from the plane-parallel plate without being totally reflected at the second plane surface. Accordingly, contrast increases, and an image of projections on the uneven object can be formed even more clearly.

If a total reflection preventing device is provided on the surface of the trap transparent member which is opposite to the surface thereof which is in close contact with the plane-parallel plate, the thickness of the trap transparent member can be reduced to a considerable extent, and thus the apparatus can be made compact. In addition, by incorporating a distortion correcting optical system into the image-forming device, distortion of an image to be formed is corrected, and an image of an accurate pattern can be clearly formed.

While the invention has been described by reference to specific embodiments chosen for purposes of illustration, it should be apparent that numerous modifications could be made thereto by those skilled in the art without departing from the basic concept and scope of the invention.

We claim:

1. A device for forming an image of an uneven surface of an object, the device comprising:

a plane-parallel plate having a pair of parallel plane surfaces and which is made of a material transparent to illuminating light, said plane-parallel plate having a refractive index larger than that of water and designed so that the uneven surface of the object is placed in close contact with a first one of said pair of plane surfaces;

a light source to generate the illuminating light to illuminate the uneven surface of the object through said plane-parallel plate; and image-forming means for forming the image of the uneven surface of the object and including a reflecting surface formed at a tilt on a first side surface of said plane-parallel plate, so that among light rays scattered back into said plane-parallel plate by the uneven surface of the object, only light that impinges on a second one of said pair of plane surfaces of said plane-parallel plate at an angle which is larger than a critical angle at a boundary between the first plane surface of said plane-parallel plate and water and that is totally reflected at the second plane surface of said plane-parallel plate is reflected back into said plane-parallel plate by said reflecting surface in a direction parallel to said pair of plane surfaces so as to be imaged by said image-forming means.

2. The device according to claim 1, wherein said plane-parallel plate is disposed between the object and said light source.

3. The device according to claim 1, wherein said light source emits monochromatic light.

4. The device according to claim 1, wherein said image-forming means further includes an image-forming lens provided on a second side surface of said plane-parallel plate opposite to the first side surface thereof provided with said reflecting surface.

5. The device according to claim 4, further comprising a solid-state image device having an image receiving surface disposed at a position where the image of the uneven surface of the object is formed by said image-forming means.

6. The device according to claim 5, wherein said image-forming means includes a mirror for reflecting the illuminating light emanating from said image-forming lens toward the image receiving surface of said solid-state imaging device.

7. The device according to claim 1, wherein said image-forming means includes an optical system for correcting distortion of the image of the uneven surface of the object.

8. A device for forming an image of an uneven surface of an object, the device comprising:

a plane-parallel plate having a pair of parallel plane surfaces and which is made of a first material transparent to illuminating light, said plane-parallel plate having a refractive index larger than that of water and designed so that the uneven surface of the object is placed in close contact with a first one of said pair of plane surfaces;

a trap transparent member made of a second material transparent to the illuminating light and having a refractive index intermediate between those of water and said plane-parallel plate, said trap transparent member being in close contact with a second one of said pair of plane surfaces of said plane-parallel plate;

a light source to generate the illuminating light to illuminate the uneven surface of the object through said plane-parallel plate; and means for forming the image of the uneven surface of the object by taking in only light that is scattered back into said plane-parallel plate by the uneven surface of the object and totally reflected at a boundary surface of said plane-parallel plate with said trap transparent member.

9. A device according to claim 8, wherein said plane-parallel plate and said trap transparent member are disposed between the object and said light source.

10. The device according to claim 8, wherein said light source emits monochromatic light.

11. The device according to claim 8, wherein said image-forming means includes a reflecting surface formed at a tilt on a first side surface of said plane-parallel plate so that light that is totally reflected at the second plane surface of said plane-parallel plate is reflected back into said plane-parallel plate in a direction parallel to said pair of plane surfaces by said reflecting surface.

12. The device according to claim 11, wherein said image-forming means further includes an image-forming lens provided on a second side surface of said plane-parallel plate opposite to the first side surface thereof provided with said reflecting surface.

13. The device according to claim 12, further comprising a solid-state imaging device having an image receiving surface disposed at a position where the image of the uneven surface of the object is formed by said image-forming means.

14. The device according to claim 13, wherein said image-forming means includes a mirror for reflecting the illuminating light emanating from said image-forming lens toward the image receiving surface of said solid-state imaging device.

15. The device according to claim 8, wherein said image-forming means includes an optical system for correcting distortion of the image of the uneven surface of the object.

16. The device according to claim 8, further comprising means for regulating a direction in which the illuminating light that enters said trap transparent member from said plane-parallel plate after being reflected by the uneven surface of the object emerges from said trap transparent member.

17. The device according to claim 16, wherein said emergence direction regulating means is a reflecting surface for reflecting the illuminating light entering said trap transparent member from said plane-parallel plate in a direction approximately parallel to said pair of plane surfaces of said plane-parallel plate.

18. The device according to claim 16, wherein said emergence direction regulating means is a tilted surface for allowing the illuminating light entering said trap transparent member from said plane-parallel plate after being reflected by the uneven surface of the object to emerge therefrom without being reflected at an inner surface of said trap transparent member.

19. The device according to claim 8, further comprising total reflection preventing means provided on a first surface of said trap transparent member which is opposite to a second surface thereof which is in contact with said plane-parallel plate.

20. The device according to claim 19, wherein said total reflection preventing means is a diffraction grating.

* * * * *